United States Patent
Tanaka et al.

(10) Patent No.: US 8,961,411 B2
(45) Date of Patent: Feb. 24, 2015

(54) INDICATION DEVICE

(75) Inventors: Naofumi Tanaka, Tokyo (JP);
Kazuyuki Kojima, Tokyo (JP); Toru Omata, Tokyo (JP); Toshio Takayama, Tokyo (JP); Yukio Kosugi, Tokyo (JP)

(73) Assignees: National University Corporation Tokyo Medical and Dental University, Tokyo (JP); Tokyo Institute of Technology, Tokyo (JP)

( * ) Notice: Subject to any disclaimer, the term of this patent is extended or adjusted under 35 U.S.C. 154(b) by 217 days.

(21) Appl. No.: 13/259,057

(22) PCT Filed: Mar. 26, 2010

(86) PCT No.: PCT/JP2010/055448
§ 371 (c)(1),
(2), (4) Date: Nov. 1, 2011

(87) PCT Pub. No.: WO2010/110450
PCT Pub. Date: Sep. 30, 2010

(65) Prior Publication Data
US 2012/0041273 A1 Feb. 16, 2012

(30) Foreign Application Priority Data

Mar. 26, 2009 (JP) ................................. 2009-077066

(51) Int. Cl.
*A61B 1/06* (2006.01)
*A61B 17/34* (2006.01)
*A61B 17/00* (2006.01)
*A61B 19/00* (2006.01)

(52) U.S. Cl.
CPC ....... *A61B 17/3403* (2013.01); *A61B 17/00234* (2013.01); *A61B 17/3421* (2013.01); *A61B 19/201* (2013.01); *A61B 19/5202* (2013.01); *A61B 2019/202* (2013.01)
USPC ........................................................ 600/249

(58) Field of Classification Search
CPC .. A61B 1/00096; A61B 1/00183; A61B 1/06; A61B 1/0607; A61B 1/0615; A61B 1/0623; A61B 1/0669; A61B 1/0676; A61B 1/0684; A61B 1/0692; A61B 1/041; A61B 1/00177; A61B 18/24; A61B 18/20; A61B 18/22; A61B 2018/2272; A61B 2018/00023; A61B 2018/2283; A61B 19/5202
USPC .......... 606/2, 10, 11, 13, 14, 17, 18; 600/160, 600/170, 171, 173, 174, 176–182, 199, 223, 600/241, 245–249
See application file for complete search history.

(56) References Cited

U.S. PATENT DOCUMENTS

| | | | |
|---|---|---|---|
| 6,044,291 A | 3/2000 | Roeckseisen | |
| 6,701,181 B2* | 3/2004 | Tang et al. | 600/478 |

(Continued)

FOREIGN PATENT DOCUMENTS

| | | |
|---|---|---|
| JP | 07-132124 | 5/1995 |
| JP | 2002-204773 | 7/2002 |
| JP | 2008-192140 | 8/2008 |

OTHER PUBLICATIONS

Supplementary European Search Report issued Jul. 30, 2013 in related European Patent Appl. No. 10756246.4.

*Primary Examiner* — Pedro Philogene
*Assistant Examiner* — Lynnsy Summitt
(74) *Attorney, Agent, or Firm* — Berliner & Associates

(57) ABSTRACT

The object is to seek a position for an insertion opening through which a treatment tool inserted inside a body cavity may reach an affected area while avoiding an obstacle. A first light emitting portion placed in an insertion portion applies light to an affected area inside a body cavity. A second light emitting portion placed in the insertion portion applies light to an inner wall of the body cavity toward the opposite side of the first light emitting portion. At this time, a light pathway on which the light from the first light emitting portion and the second light emitting portion will not strike the obstacle (e.g., an organ outside than the affected area, etc.) inside the body cavity is searched for. By making, in the position that the light from the second light emitting portion strikes, an insertion opening for inserting a treatment tool, the treatment tool can reach the affected area without interfering with the obstacle.

2 Claims, 7 Drawing Sheets

(56) References Cited

U.S. PATENT DOCUMENTS

| | | | |
|---|---|---|---|
| 2003/0120130 A1* | 6/2003 | Glukhovsky et al. | 600/109 |
| 2006/0242884 A1 | 11/2006 | Talieh | |
| 2007/0270651 A1* | 11/2007 | Gilad et al. | 600/160 |
| 2008/0186693 A1 | 8/2008 | White | |

* cited by examiner

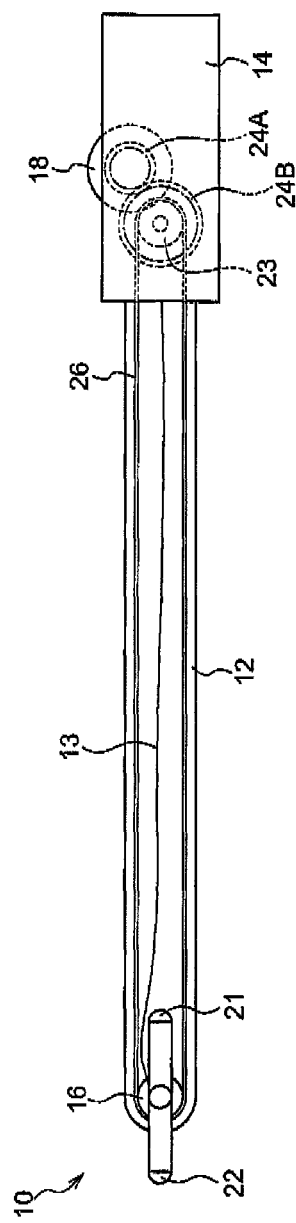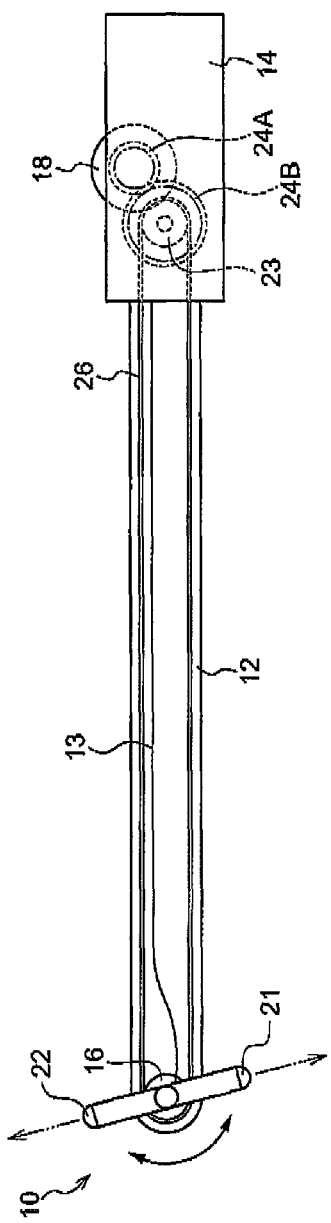

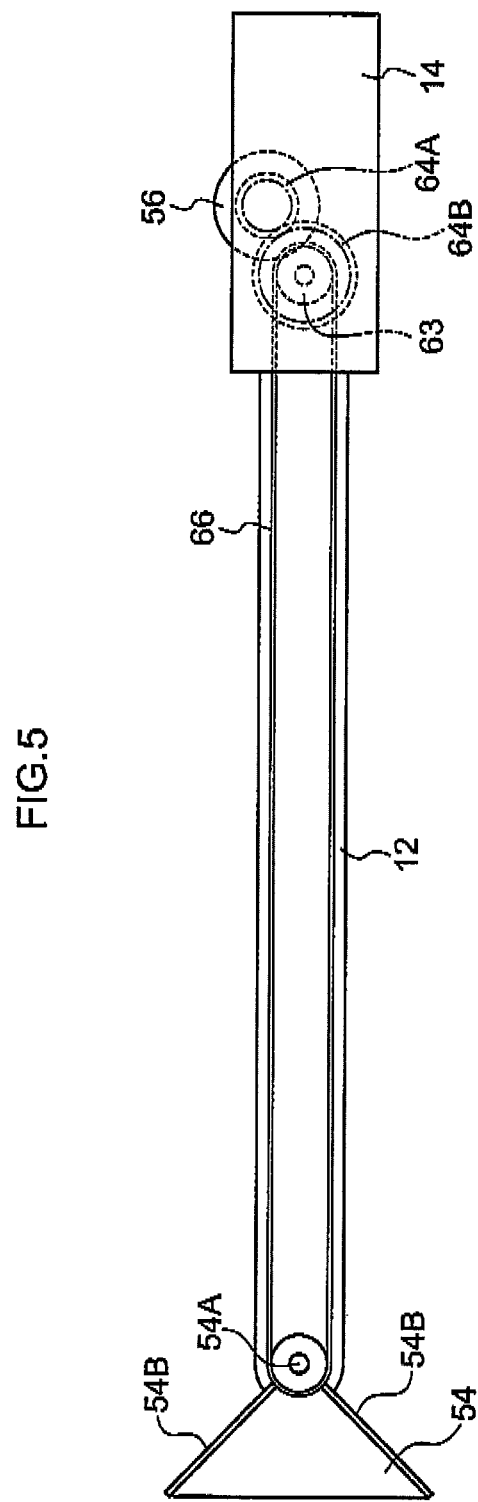

INDICATION DEVICE

TECHNICAL FIELD

The present invention relates to an indication device that indicates a position for an insertion opening for inserting a treatment tool into a body cavity.

BACKGROUND ART

In patent document 1, laser forceps for abdominal cavity surgery is disclosed. In the laser forceps for abdominal cavity surgery disclosed in patent document 1, an operator increases the gap between a contact chip 12 and a hook 141 by operating an operation lever 15 in the direction of arrow C. The operator hooks an affected area that is the target of the surgical procedure in such a way that the affected area enters this gap. The operator holds the affected area between the hook and the contact chip by operating the operation lever in the direction of arrow D until the gap becomes small. An appropriately adjusted laser is supplied from an optical fiber 13 to the contact chip, and the laser is applied to the affected area. Moreover, if necessary, the operator presses the hook against the contact chip in such a way as to make the gap small and excises the affected area. The laser also performs hemostasis at the time of the excision.

Patent Document 1: JP-A No. 7-132124 (FIG. 1)

SUMMARY OF INVENTION

Technical Problem

Incidentally, in the case of inserting a treatment tool such as forceps into the abdominal cavity to perform a procedure such as an excision with respect to an affected area, it is necessary for the treatment tool to not interfere with another organ. That is, in the case of a linear treatment tool, for example, it is necessary for no other organ to be on the straight line joining the insertion opening for inserting the treatment tool and the affected area.

Conventionally, the treatment tool has sometimes ended up interfering with an organ outside the affected area, because the position for the insertion opening for inserting the treatment tool has been estimated from an image shot by an endoscope inserted inside the abdominal cavity.

In consideration of the above-described facts, the object of the present invention is to seek a position for an insertion opening through which a treatment tool inserted inside a body cavity can reach an affected area while avoiding an obstacle.

Solution to Problem

An indication device of a first aspect of the present invention includes: an insertion portion capable of being inserted inside a body cavity; a first application portion, placed at the insertion portion, capable of applying light to an affected area inside the body cavity; and a second application portion, placed at the insertion portion, capable of applying light to an inner wall inside the body cavity toward the opposite side of the first application portion.

According to this configuration, the insertion portion is inserted inside the body cavity. The first application portion placed at the insertion portion applies light to the affected area inside the body cavity. The second application portion placed at the insertion portion applies light to the inner wall of the body cavity toward the opposite side of the first application portion.

At this time, a light pathway on which the light from the first application portion and the second application portion will not strike an obstacle (e.g., an organ outside than the affected area, etc.) inside the body cavity is searched for. By making, in the position that the light from the second light emitting portion strikes, an insertion opening for inserting a treatment tool, the treatment tool may reach the affected area without interfering with an obstacle.

In this way, according to the indication device of the first aspect of the present invention, a position for an insertion opening through which a treatment tool inserted inside a body cavity may reach an affected area while avoiding an obstacle may be sought.

An indication device of a second aspect is the indication device of the first aspect of the present invention, wherein the first application portion is a first light emitting portion placed at a distal end portion of the insertion portion and self-emits light, and the second application portion is a second light emitting portion placed at the distal end portion of the insertion portion on the opposite side of the first application portion and self-emits light.

According to this configuration, the first light emitting portion placed at the distal end portion of the insertion portion self-emits light, and applies the light to the affected area inside the body cavity. The second light emitting portion placed at the distal end portion of the insertion portion on the opposite side of the first light emitting portion self-emits light, and applies the light to the inner wall of the body cavity toward the opposite side of the first light emitting portion.

In this way, the light source may be placed and the light may be applied inside the body cavity, so compared to a configuration where the light source is placed outside the body cavity, the intensity of the light reaching the inner wall becomes stronger and the position where the insertion opening is to be made is easy to check.

An indication device of a third aspect is the indication device of the second aspect, further including a rotating body, disposed rotatably at the distal end portion of the insertion portion and in which the first light emitting portion and the second light emitting portion are placed and a rotation operation portion disposed on a rear end portion side of the insertion portion, that enables rotation operation of the rotating body.

According to this configuration, rotation operation of the rotating body may be performed by the rotation operation portion disposed on the rear end portion of the insertion portion. Because of this, by changing the angle of rotation of the rotating body, the application direction of the first light emitting portion and the second light emitting portion placed in the rotating body may be adjusted and a pathway that may avoid an obstacle is easy to search for.

An indication device of a fourth aspect is the indication device of the first aspect of the present invention, wherein the first application portion and the second application portion are configured to include a light source, disposed at a rear end portion of the insertion portion, that applies light toward a distal end portion of the insertion portion, and a light splitting portion, placed at the distal end portion of the insertion portion, that splits the light from the light source in one direction and the opposite side thereof.

According to this configuration, the light source disposed in the rear end portion of the insertion portion applies light toward the distal end portion of the insertion portion. The light from this light source is split in one direction and the opposite side thereof by the light splitting portion.

In this configuration, the light source may be positioned outside the body cavity and the light may be applied to the light splitting portion inside the body cavity and split, so the light source does not have to be put inside the body cavity.

An indication device of a fifth aspect is the indication device of the fourth aspect, wherein the fight splitting portion is disposed rotatably in the insertion portion, and a rotation operation portion that enables rotation operation of the light splitting portion is disposed on the rear end portion side of the insertion portion.

According to this configuration, rotation operation of the light splitting portion may be performed by the rotation operation portion disposed on the rear end portion of the insertion portion. Because of this, by changing the angle of rotation of the light splitting portion, the application direction of the light split by the light splitting portion may be adjusted, and a pathway that may avoid an obstacle is easy to search for.

In order to solve the problem of seeking a position for an insertion opening through which a treatment tool inserted inside a body cavity may reach an affected area while avoiding an obstacle, a position deciding method including the following steps may also be used.

This position deciding method includes: an insertion step of inserting an insertion portion inside a body cavity; and an application step of applying light to an affected area inside the body cavity from the insertion portion inserted in the insertion step, applying, toward the opposite side of that light, light from the insertion portion to an inner wall inside the body cavity, and making an insertion opening for a treatment tool in the place of application on the inner wall.

In the application step, the light path on which the light is applied to the affected area from the insertion portion and the light path on which the light is applied to the inner wall from the insertion portion become a pathway in which there is no obstacle on those light paths. Consequently, by inserting the treatment tool through the insertion opening for the treatment tool decided in the application step, the treatment tool may reach the affected area without interfering with an obstacle. In this way, according to the position deciding method, a position for an insertion opening through which a treatment tool inserted inside a body cavity may reach an affected area while avoiding an obstacle may be sought.

Advantageous Effect of Invention

The present invention takes the above-described configurations, so a position for an insertion opening through which a treatment tool inserted inside a body cavity may reach an affected area while avoiding an obstacle may be sought.

BRIEF DESCRIPTION OF THE DRAWINGS

FIG. 1A is a schematic view showing the configuration of an indication device according to a first embodiment;

FIG. 1B is a schematic view showing the configuration of the indication device according to the first embodiment;

FIG. 5 is a schematic view showing the configuration of a rotation mechanism that rotates a beam splitter in the indication device according to the second embodiment;

DESCRIPTION OF EMBODIMENTS

Examples of embodiments according to the present invention will be described below on the basis of the drawings.
(Configuration of Indication Device According to First Embodiment)

Figure 2:
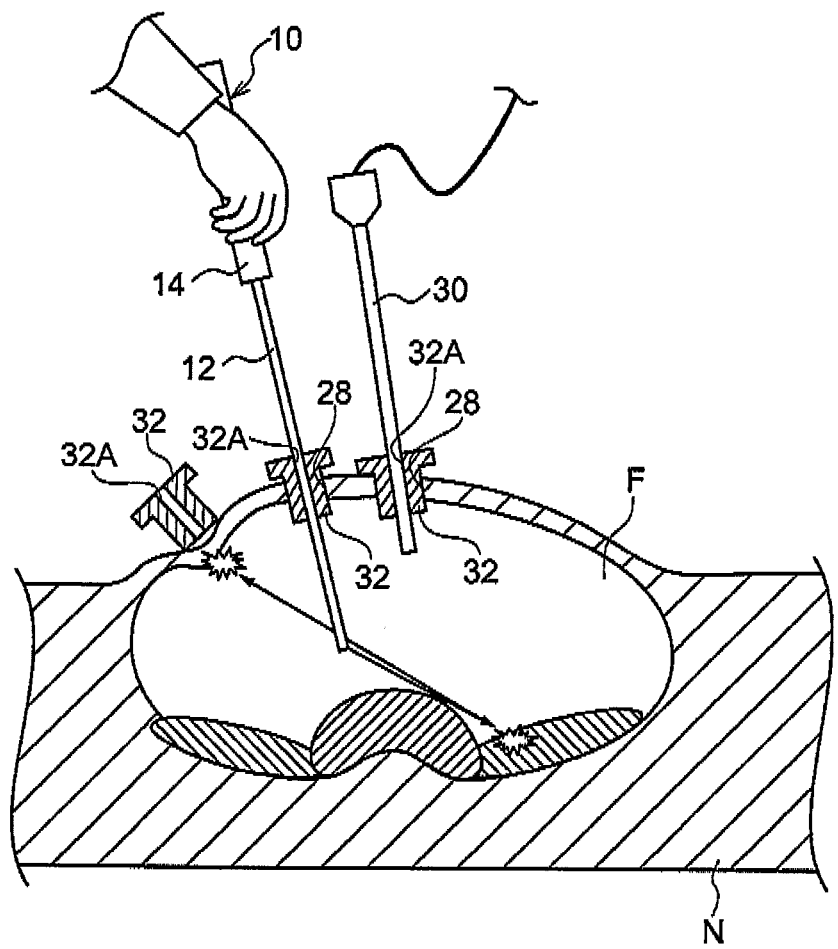
FIG. 2 is a partial sectional view showing a state of use of the indication device according to the first embodiment, with a torso being cut in a vertical direction (a craniocaudal direction)
Figure 3:
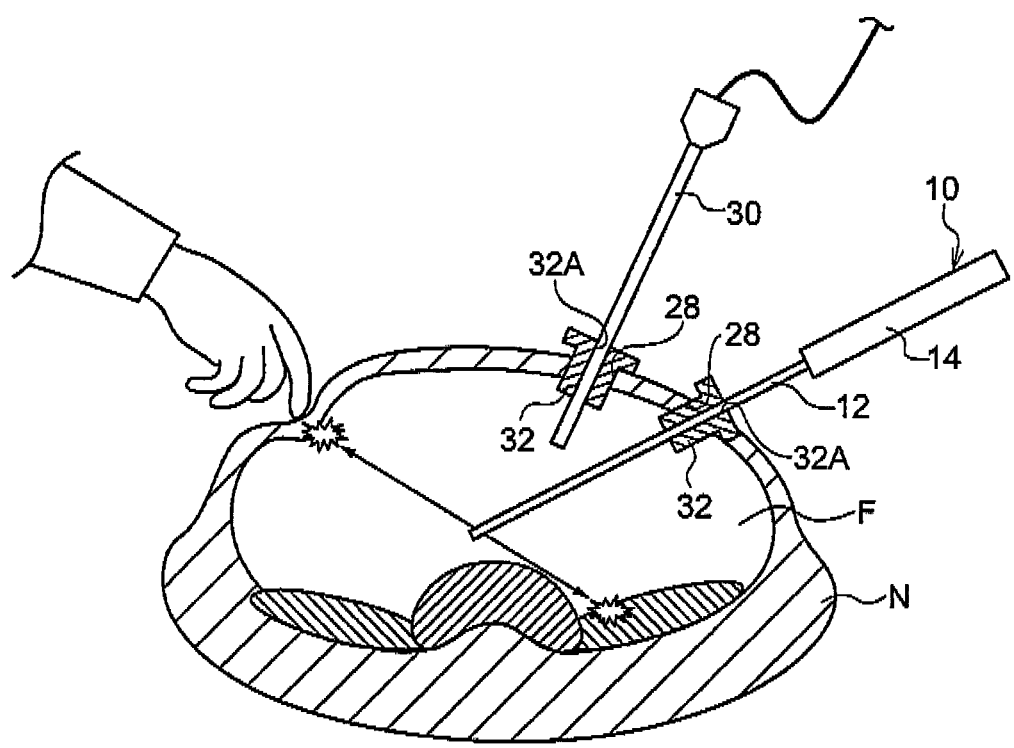
FIG. 3 is a partial sectional view showing a state of use of the indication device according to the first embodiment, with the torso being cut in a horizontal direction (a direction orthogonal to the craniocaudal direction)

First, the configuration of an indication device 10 according to a first embodiment will be described. FIG. 1 are drawings showing the configuration of the indication device 10 according to the first embodiment. FIG. 2 and FIG. 3 are drawings showing a state of use of the indication device 10 according to the first embodiment.

As shown in FIG. 1A and FIG. 2, the indication device 10 according to the first embodiment is equipped with a rod-like insertion portion 12 that is inserted inside an abdominal cavity F of a human (patient) N. A rod-like operation portion 14 that enables operation of the insertion portion 12 is disposed continuously on a rear end portion (proximal end portion) of the insertion portion 12. Specifically, an operator (doctor) can adjust the amount of insertion of the insertion portion 12 inside the abdominal cavity F by gripping the operation portion 14 and inserting and removing the operation portion 14. Further, the operator can adjust the inclination of the insertion portion 12 by gripping the operation portion 14 and changing the inclination of the operation portion 14. Further, the operator can adjust the position of rotation of the insertion portion 12 about its axial direction by gripping the operation portion 14 and rotating the operation portion 14 about its axial direction.

The site into which the insertion portion 12 is inserted is not limited to being the abdominal cavity F, and may also be a chest cavity or the like; it suffices for the site to be a body cavity.

As shown in FIG. 1B, a rotating body 16 is rotatably disposed on a distal end portion of the insertion portion 12. A rotation operation portion 18 that enables rotation operation of the rotating body 16 is disposed at the operation portion 14 positioned on the rear end portion of the insertion portion 12.

A gear 24A, a gear 24B, a pulley 23, and a wire 26 are placed, as examples of transmission members that transmit the rotational force of the rotation operation portion 18 to the rotating body 16, between the rotation operation portion 18 and the rotating body 16. In the present embodiment, when the operator rotates the rotation operation portion 18, the gear 24A disposed coaxially with a rotating shaft of the rotation operation portion 18 rotates integrally with the rotation operation portion 18. When the gear 24A rotates, the gear 24B meshed with the gear 24A rotates, and the pulley 23 disposed coaxially with a rotating shaft of the gear 24B rotates integrally with the gear 24B. When the pulley 23 rotates, the endless wire 26 wrapped around the pulley 23 and the rotating body 16 rotates (cyclically moves), and the rotating body 16 rotates. Note that, the transmission members that transmit the rotational force of the rotation operation portion 18 to the rotating body 16 are not limited to those described above, and various machine elements may be used.

A first light emitting portion 21 that self-emits light is placed on the rotating body 16. A second light emitting portion 22 that self-emits light is placed on the rotating body 16 on the opposite side of the first light emitting portion 21. An electric cable 13 for supplying electric power to the second light emitting portion 22 and the first light emitting portion 21 is placed inside the insertion portion 12.

The first light emitting portion 21 applies light in one direction, and the second light emitting portion 22 applies light to the opposite side of the application direction of the first light emitting portion 21. Due thereto, the light from the first light emitting portion 21 is made capable of being applied to an affected area, and, when the light from the first light emitting portion 21 has been applied to the affected area, the light from the second light emitting portion 22 becomes capable of being applied to an inner wall inside the abdominal cavity F.

In the present embodiment, the light path of the light applied from the first light emitting portion 21 and the light path of the light applied from the second light emitting portion 22 form a straight line. This is because treatment tools such as forceps are formed in a straight line, and treatment tools follow a course linearly from an open hole to an affected area.

Consequently, it is desirable for the light path of the light applied from the first light emitting portion 21 and the light path of the light applied from the second light emitting portion 22 to be defined in accordance with the shape of the treatment tool. Thus, the indication device may also have a configuration where the light path of the light applied from the first light emitting portion 21 and the light path of the light applied from the second light emitting portion 22 do not form a straight line; for example, the light path of the light applied from the first light emitting portion 21 and the light path of the light applied from the second light emitting portion 22 may also be parallel. Further, the light path of the light applied from the second light emitting portion 22 may also have an angle with respect to the light path of the light applied from the first light emitting portion 21.

(Operation of Indication Device 10 According to First Embodiment)

Next, the operation of the indication device 10 according to the first embodiment will be described.

Here, a case of performing a lymphadenectomy in stomach cancer surgery will be taken as an example and described. The indication device 10 in the present embodiment may also be used for purposes other than stomach cancer surgery.

First, at least two open holes 28 are formed in the abdominal region. Trocars 32, in which are formed insertion openings 32A for inserting a treatment tool, an endoscope 30, and the indication device 10, etc., are attached to these two open holes 28.

The endoscope 30 is inserted into the insertion opening 32A in one of the trocars 32, and the indication device 10 is inserted into the insertion opening 32A in the other of the trocars 32. At this time, the operator grips the operation portion 14 of the indication device 10, and the insertion portion 12 of the indication device 10 is inserted inside the abdominal cavity F.

The operator uses the operation portion 14 to operate the insertion portion 12 while using the endoscope 30 to check the position of the distal end portion of the insertion portion 12. Further, the operator uses the rotation operation portion 18 to rotate the rotating body 16 and adjust the direction in which the first light emitting portion 21 and the second light emitting portion 22 apply light, so that the light from the first light emitting portion 21 is applied to the affected area and the light from the first light emitting portion 21 and the second light emitting portion 22 is not applied to the spleen or the pancreas that becomes an obstacle.

At this time, the position on the inner wall at which the light from the second light emitting portion 22 is being applied becomes a position at which the operator forms an open hole 28 for attaching a trocar 32 into which a treatment tool such as forceps is inserted. The operator views from outside the position at which the light from the second light emitting portion 22 is being applied and seeks the open hole position. At this time, as shown in FIG. 3, the operator applies pressure with a finger on the abdominal region from outside the abdominal region, and observes the deformation at the application point on the abdominal wall, whereby the operator accurately locates the application point.

Next, at this application point, the operator forms an open hole in the abdominal wall, and attaches a trocar 32 to this open hole. A treatment tool such as forceps is inserted inside the abdominal cavity F through the insertion opening 23A in this trocar 32, and a lymph node is excised by that treatment tool.

The treatment tool can excise the lymph node, without interfering with the spleen or the pancreas, by following the light path of the light from the first light emitting portion 21 and the second light emitting portion 22.

In this way, by making, in the position that the light from the second light emitting portion 22 strikes, an insertion opening for inserting the treatment tool, the treatment tool can reach the affected area without interfering with an obstacle.

The present invention is not limited to the embodiment described above and is capable of various modifications, changes, and improvements.

(Configuration of Indication Device According to Second Embodiment)

Next, the configuration of an indication device 50 according to a second embodiment will be described. The same reference numerals will be given to portions that are the same as those of the indication device 10 described above.

Whereas in the indication device 10 described above, the first light emitting portion 21 and the second light emitting portion 22 that are light sources were disposed in the insertion portion 12 that is inserted inside the body cavity, the indication device 50 according to the second embodiment is given a configuration in which the light sources are capable of being positioned and used outside the body cavity.

Figure 4A:
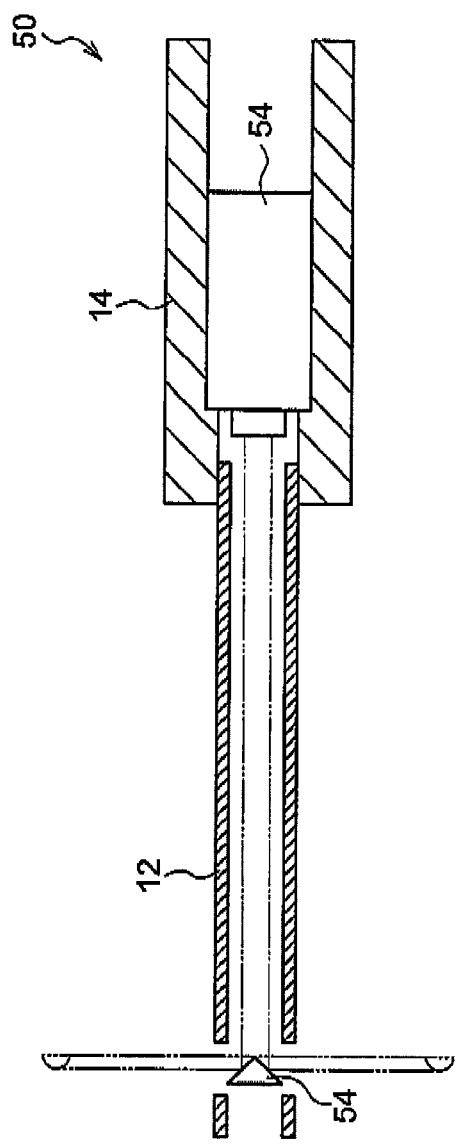
FIG. 4A is a schematic view showing the configuration of an indication device according to a second embodiment.

As shown in FIG. 4A, the indication device 50 according to the second embodiment is equipped with a rod-like insertion portion 12 that is inserted inside an abdominal cavity of a human (patient). A rod-like operation portion 14 that enables operation of the insertion portion 12 is disposed continuously on the rear end portion (proximal end portion) of the insertion portion 12. Specifically, an operator (a doctor) can adjust the amount of insertion of the insertion portion 12 inside the abdominal cavity by gripping the operation portion 14 and inserting and removing the operation portion 14. Further, the operator can adjust the inclination of the insertion portion 12 by gripping the operation portion 14 and changing the inclination of the operation portion 14. Further, the operator can adjust the position of rotation of the insertion portion 12 about its axial direction by gripping the operation portion 14 and rotating the operation portion 14 about its axial direction.

A light source 52 that applies light toward a distal end portion of the insertion portion 12 is disposed in the operation portion 14. A beam splitter 54, which is an optical member serving as an example of a light splitting portion that splits the light from the light source 52 in one direction and the opposite side thereof, is disposed in the distal end portion of the insertion portion 12.

Figure 4B:
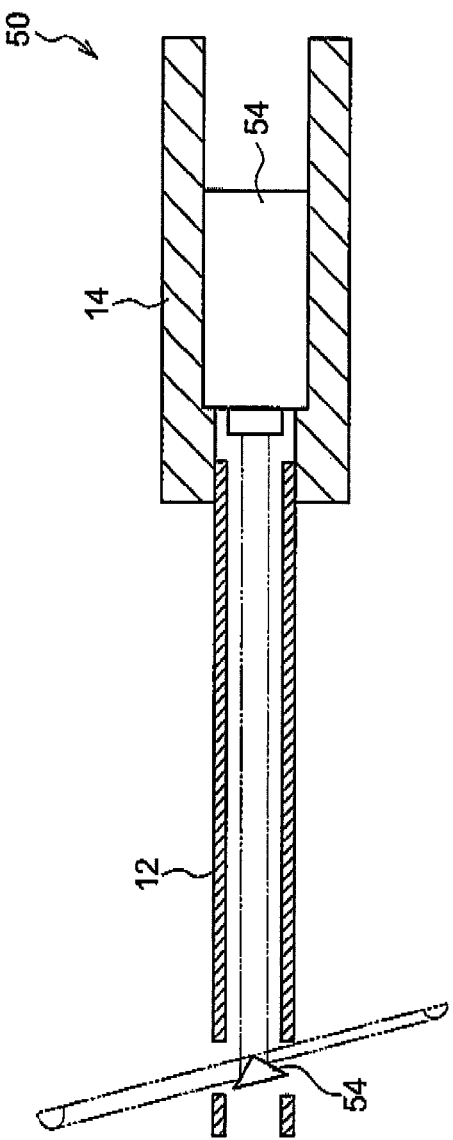
FIG. 4B is a schematic view showing the configuration of the indication device according to the second embodiment.

As shown in FIG. 4B and FIG. 5, the beam splitter 54 is disposed rotatably in the distal end portion of the insertion portion 12. A rotation operation portion 56 that enables rotation operation of the beam splitter 54 is disposed in the operation portion 14.

A gear 64A, a gear 64B, a pulley 63, and a wire 66 are placed, as examples of transmission members that transmit the rotational force of the rotation operation portion 56 to the beam splitter 54, between the rotation operation portion 56 and the beam splitter 54. In the present embodiment, when the operator rotates the rotation operation portion 56, the gear 64A disposed coaxially with a rotating shaft of the rotation operation portion 56 rotates integrally with the rotation operation portion 56. When the gear 64A rotates, the gear 64B meshed with the gear 64A rotates, and the pulley 63 disposed coaxially with a rotating shaft of the gear 64B rotates integrally with the gear 64B. When the pulley 63 rotates, the endless wire 66 wrapped around the pulley 63 and a rotating shaft portion 54A of the beam splitter 54 rotates (cyclically moves), and the beam splitter 54 rotates. The transmission members that transmit the rotational force of the rotation operation portion 56 to the beam splitter 54 are not limited to those described above, and various machine elements may be used.

The beam splitter 54 is formed in a triangular prism. The two side surfaces thereof serve as reflecting surfaces (mirror surfaces) 54B that reflect light. One of the reflecting surfaces 54B guides the light from the light source 52 in one direction, and the other of the reflecting surfaces 54B guides the light from the light source 52 in the opposite direction.

Because of this, the light reflected by the one reflecting surface 54B is made capable of being applied to the affected area, and, when that light has been applied to the affected area, the light reflected by the other reflecting surface 54B becomes capable of being applied to the inner wall inside the abdominal cavity F.

Like in the case of the first embodiment, it is possible for the light path of the light reflected by the one reflecting surface 54B and the light path of the light reflected by the other reflecting surface 54B to be defined in accordance with the shape of the treatment tool.

The indication device 50 according to the second embodiment is also used like in the case of the first embodiment, so by making, in the position that the light strikes on the inner wall, an insertion opening for inserting the treatment tool, the treatment tool can reach the affected area without interfering with an obstacle.

In the configuration of the second embodiment, the light source 52 is placed in the operation portion 14, the light source 52 can be positioned outside the body cavity, and the light can be applied through the beam splitter 54 inside the body cavity, so the light source 52, an electric cable for supplying electric power to the light source 52, and an electric circuit for generating light do not have to be inserted inside the body cavity. Further, the number of parts inserted inside the body cavity becomes fewer, and the insertion portion may be miniaturized.

Figure 6A:
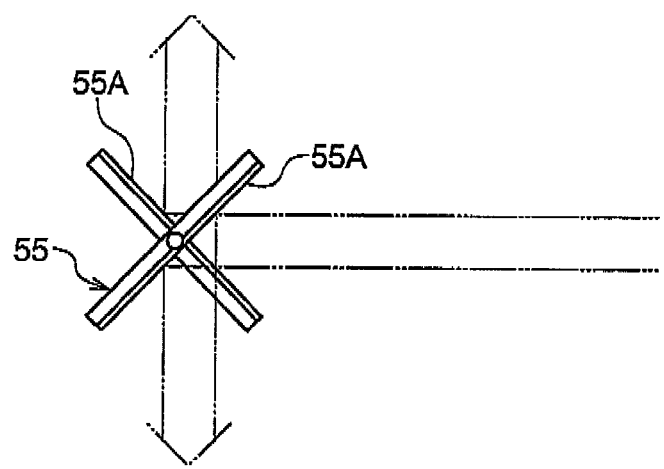
FIG. 6A is a schematic view showing the configuration of a beam splitter according to a modification example having intersecting reflecting surfaces.
Figure 6B:
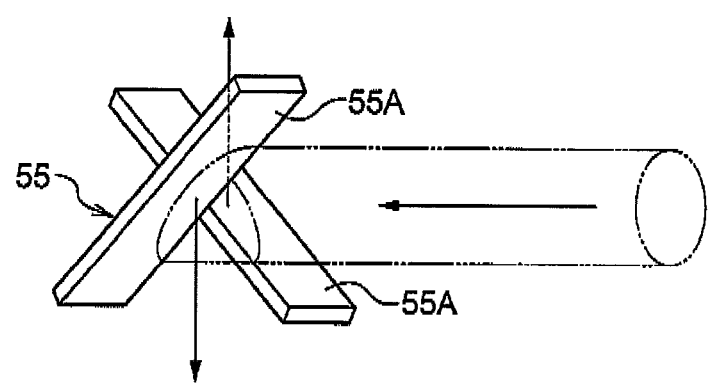
FIG. 6B is a schematic view showing the configuration of the beam splitter according to the modification example having intersecting reflecting surfaces.

As shown in FIG. 6A and FIG. 6B, the light splitting portion may also be a beam splitter 55 having intersecting reflecting surfaces (mirror surfaces) 55A. The two reflecting surfaces 55A perpendicularly intersect; one of the reflecting surfaces 55A guides the light from the light source 52 in one direction, and the other of the reflecting surfaces 55A guides the light from the light source 52 to the opposite side of the one direction.

Figure 7:
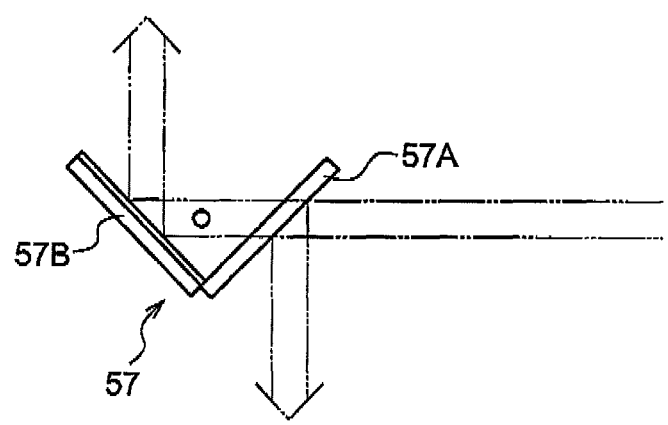
FIG. 7 is a schematic view showing the configuration of a beam splitter according to a modification example configured by a half mirror and a mirror.

Further, as shown in FIG. 7, the light splitting portion may also be a beam splitter 57 configured by a half mirror 57A and a mirror 57B. In this configuration, part of the light from the light source 52 is guided in one direction by the half mirror 57A, and the other part of the light from the light source 52 passes through the half mirror 57A and is applied to the mirror 57B. The light applied to the mirror 57B is guided to the opposite side of the one direction.

The invention claimed is:

1. An indication device comprising
a rod-like insertion portion capable of being inserted inside a body cavity;
a first application portion, placed at the insertion portion, capable of applying light in one direction toward an affected area inside the body cavity; and
a second application portion, placed at the insertion portion, capable of applying light to an inner wall inside the body cavity toward the opposite side of the application direction of the first application portion,
wherein
the first application portion is a first light emitting portion placed at a distal end portion of the insertion portion and self-emits light,
the second application portion is a second light emitting portion placed at the distal end portion of the insertion portion on the opposite side of the first application portion and self-emits light, and
the indication device includes,
a rotating body disposed rotatably at the distal end portion of the insertion portion and in which the first light emitting portion and the second light emitting portion are placed,
a rotating shaft portion, disposed at a direction orthogonal to an axial direction of the rod-like insertion portion, that becomes a center-of-rotation shaft of the rotating body, and
a rotation operation portion, disposed on a rear end portion side of the insertion portion, that enables operation of angle rotation of the rotating body,
wherein the rotating shaft portion has an axis of rotation that intersects a longitudinal axis of the rod-like insertion portion.

2. An indication device comprising:
a rod-like insertion portion capable of being inserted inside a body cavity;
a first application portion, placed at the insertion portion, capable of applying light in one direction toward an affected area inside the body cavity; and
a second application portion, placed at the insertion portion, capable of applying light to an inner wall inside the body cavity toward the opposite side of the application direction of the first application portion,
wherein
the first application portion and the second application portion are configured to include,
a light source, disposed at a rear end portion of the insertion portion, that applies light toward a distal end portion of the insertion portion and
a light splitting portion, placed at the distal end portion of the insertion portion, that splits the light from the light source in one direction and the opposite side thereof, the light splitting portion being disposed rotatably, with a rotating shaft portion disposed at a direction orthogonal to an axial direction of the rod-like insertion portion serving as its center-of-rotation shaft while maintaining an angle between the application direction of the first application portion and the application direction of the second application portion, and a rotation operation portion, disposed on the rear end portion side of the insertion portion, that enables rotation operation of the light splitting portion.

* * * * *